United States Patent [19]
Saburi et al.

[11] Patent Number: 5,296,836
[45] Date of Patent: Mar. 22, 1994

[54] GAS COMPONENT DETECTING ELEMENT AND DETECTOR

[75] Inventors: Toshiki Saburi, Ichinomiya; Masaya Fujimoto, Kariya; Tadashi Tsuruta, Nagoya; Naochika Nunogaki, Yokkaichi, all of Japan

[73] Assignee: Nippondenso Co., Ltd., Kariya, Japan

[21] Appl. No.: 952,653

[22] Filed: Sep. 28, 1992

Related U.S. Application Data

[62] Division of Ser. No. 580,970, Sep. 12, 1990, Pat. No. 5,182,136.

[30] Foreign Application Priority Data

Sep. 12, 1989 [JP] Japan ................................ 1-236328

[51] Int. Cl.$^5$ .................................................. H01C 7/00
[52] U.S. Cl. ...................... 338/34; 427/126.3; 29/610.1
[58] Field of Search ................ 338/34; 422/97, 90; 436/134, 152; 427/126.3

[56] References Cited

U.S. PATENT DOCUMENTS

| | | |
|---|---|---|
| 4,088,435 | 5/1978 | Hindin . |
| 4,249,156 | 2/1981 | Micheli . |
| 4,286,378 | 9/1981 | Micheli . |
| 4,290,399 | 10/1981 | John . |
| 4,536,241 | 8/1985 | Logothetis et al. . |
| 4,579,751 | 4/1986 | Forster . |
| 4,857,275 | 8/1989 | Furusaki et al. ................ 338/34 X |

FOREIGN PATENT DOCUMENTS

| | | |
|---|---|---|
| 55-74452 | 6/1980 | Japan . |
| 56-112638 | 9/1981 | Japan . |
| 59-37779 | 9/1984 | Japan . |

OTHER PUBLICATIONS

Journal of American Chemical Society, May 23, 1979, 101, 11, pp. 2870–2875, Horsley "A Molecular Orbital Study of String Metal–Support Interaction Between Platinum and Titanium Dioxide".

Journal of Catalysis 59, pp. 293–302, 1979 Baker et al. "Electron Microscopy of Supported Metal Particles".

Primary Examiner—Marvin M. Lateef
Attorney, Agent, or Firm—Cushman, Darby & Cushman

[57] ABSTRACT

A gas component detecting element using particles of metal oxide. The particles are prepared and calcined, and then subjected to a treatment which enlarges a specific surface area thereof. Catalyst particles are supported on the surface of these particles, and then the particles are sintered. The gas component detecting element is formed from these particles. A detector formed in this way can be used for a long period of time without any change in characteristics.

5 Claims, 9 Drawing Sheets

GAS COMPONENT DETECTING ELEMENT AND DETECTOR

This is a division of application Ser. No. 07/580,970, filed Sep. 12, 1990, now U.S. Pat. No. 5,182,136 issued Jan. 26, 1993.

BACKGROUND OF THE INVENTION

The present invention relates to a method for producing a gas component detecting element and a detector.

Hitherto, it has been known to use a gas component detecting element comprising titanium dioxide for indirect detection of air-fuel ratio of internal-combustion engine. According to this known method which utilizes the property of titanium dioxide to change in its electrical resistance depending on concentration of the gas component, concentration of the gas component is detected by the change of electrical resistance and air-fuel ratio of internal-combustion engine is indirectly detected based on the detected concentration of gas component.

In the case of this gas component detecting element comprising titanium dioxide, titanium dioxide alone is slow in adsorption and resorption of gas component and so low in sensitivity and therefore, conventionally a platinum/rhodium catalyst was supported on the surface of titanium dioxide particles for enhancement of sensitivity (e.g., Japanese Patent Kokai No. 56-112638).

Internal-combustion engine is used at temperatures in a very wide range (200°–1000° C.). Therefore, particles of the platinum/rhodium catalyst easily move about on the surface of titanium dioxide particles and they gather and agglomerate to result in growth of particles due to especially the heat under high temperature.

As a result, catalytically active area on the surface of titanium dioxide particles decreases and absorption and resorption of gas component on the surface of titanium dioxide particles become slow to cause reduction of sensitivity for gas component.

The inventors have conducted intensive research on these points and have found out the cause for movement of catalyst particles under high temperature. That is, it is guessed that catalyst particles firmly bond to surface defect (called active point) of titanium dioxide particles with bonding of S.M.S.I. (Strong Metal Support Interaction) as disclosed, for example, in "American Chemical Society", pages 2870–2874 published in U.S.A. in 1979. The surface defect of titanium dioxide means lattice defect caused by escaping, from crystal lattice, of unpaired electrons (dangling bond), oxygen or the like on the surface of titanium dioxide. Bonding to such surface defect results in strong adherence of the surface of titanium dioxide particles and catalyst particles.

However, the surface defects (active points) of titanium dioxide particles disappear owing to reduction of specific surface area accompanied by growth of particles, and bonding of defects to each other and rearrangement of defects by the heat at heat treatment, namely, calcination which is a pretreatment for stably obtaining the final desired product, namely, titanium dioxide sintered body (for reducing heat shrink and obtaining desired density). Thus, the surface defect density markedly decreases.

As a result, even if catalyst particles is supported on titanium dioxide particles having a low surface defect density, proportion of catalyst particles which bond to the surface defects is very small and thus movement of catalyst particles is brought about due to heat.

The present invention aims at inhibition of particle growth by preventing movement of catalyst particles.

SUMMARY OF THE INVENTION

The present invention has been accomplished by the research conducted by the inventors in view of the above problems and includes the technical means of calcining titanium dioxide particles, increasing the amount of surface defects on the surface of the calcined titanium dioxide than the amount of surface defects before calcination, supporting a catalyst on the surface of titanium dioxide subjected to the above treatment, and sintering the titanium dioxide particles having the catalyst supported thereon.

That is, the present invention provides the following method for producing a gas component detecting element and the following detector.

(1) A method for producing a gas component detecting element for detectors which comprises a sintered body of particles of a metal oxide which changes in its electrical resistance depending on relative atmosphere of combustible components in an exhaust gas, catalyst particles being supported on the surface of particles of the metal oxide, the method comprising the following steps:

preparing particles of the metal oxide, calcining particles of the metal oxide, subjecting the calcined particles to a treatment for enlarging specific surface area of the calcined particles, supporting catalyst particles on the surface of the particles subjected to the enlargement treatment, and sintering the particles on which the catalyst particles are supported.

(2) A method for producing a gas component detecting element for detectors which comprises a sintered body of particles of titanium dioxide which change in its electrical resistance depending on relative atmosphere of combustible components in an exhaust gas, catalyst particles being supported on the surface of the particles of titanium dioxide, the method comprising the following steps:

preparing particles of titanium dioxide, calcining the particles of titanium dioxide, subjecting the calcined particles of titanium dioxide to a grinding treatment so that ratio specific surface area ($A_1$) of the particles of titanium dioxide at calcination before grinding and specific surface area ($A_2$) of the particles of titanium dioxide after grinding satisfies the relation $A_1/A_2 < 1.0$, supporting catalyst particles on the surface of the particles of titanium dioxide subjected to grinding treatment, and sintering the particles of titanium dioxide on which the catalyst particles are supported.

(3) A method for producing a gas component detecting element for detectors which comprises a sintered body of particles of titanium dioxide which changes in its electrical resistance depending on relative atmosphere of combustible components in an exhaust gas, catalyst particles being supported on the surface of the particles of titanium dioxide, the method comprising the following steps:

preparing particles of titanium dioxide, calcining the particles of titanium dioxide, subjecting the calcined particles of titanium dioxide to a grinding treatment so that ratio of specific surface area ($A_1$) of the particles of titanium dioxide at calcination before grinding and specific surface area ($A_2$) of the particles of titanium dioxide after grinding satisfies the relation $A_1/A_2 < 1.0$, impregnating the particles of titanium dioxide subjected to grinding treatment with a mixed solution of chloroplatinic acid and rhodium chloride, adding an organic binder to the particles of titanium dioxide impregnated with the mixed solution to produce a paste, provided on the surface of a substrate the pasty particles of titanium dioxide in the form of a film of a given thickness, and sintering the pasty particles of titanium dioxide provided on the surface of substrate at 800°-1300° C.

(4) A detector which has a gas component detecting element comprising a sintered body of particles of a metal oxide which changes in its electrical resistance depending on relative atmosphere of combustible components in an exhaust gas, catalyst particles being supported on the particles of metal oxide wherein the catalyst particles comprise fine catalyst particles of about 1 nm-about 30 nm and coarse catalyst particles of at least about 100 nm, the fine catalyst particles and the coarse catalyst particles are supported on the particles of metal oxide.

BRIEF DESCRIPTION OF THE DRAWINGS

FIG. 13 and FIG. 14(a) and (b) show a sensor structure of one example of the present invention.

DETAILED DESCRIPTION OF THE INVENTION

Method for increasing amount of the surface defects includes, for example, grinding particles of titanium dioxide or dissolving the surface of particles of titanium dioxide with inorganic acid or organic acid.

When particles of titanium dioxide are ground, fresh faces are produced at the surface of ground particles. At the fresh faces, unpaired electrons are formed because the portion at which particles are bonded to each other is forcedly torn off by the grinding. For this reason, amount (density) of surface defects increases.

Ratio of specific surface area of the surface of particles of titanium dioxide before and after grinding has the relation of (specific surface area before grinding/specific surface area after grinding) < 1.0. That the above ratio is smaller than 1.0 means that specific surface are after grinding is larger than that before grinding and as a result, amount of surface detects of titanium dioxide increases.

On the other hand, dissolution of the surface of particles of titanium dioxide with inorganic acids such as hydrochloric acid, nitric acid, phosphoric acid and hydrofluoric acid or organic acids results in fresh faces on that surface and for the same reason as above, amount of surface defects of titanium dioxide increases.

The metal oxide which changes in its electrical resistance according to the relative atmosphere of combustible component in exhaust gas includes, for example, cobalt oxide, tin oxide, nickel oxide, zinc oxide and the like as well as titanium dioxide and any of them can be used in the present invention.

The catalyst used in the present invention is an oxidation catalyst and it may comprise a platinum/rhodium mixture or this mixture to which is added at least one metal selected from the group consisting of noble metals such as rhodium, palladium, and iridium, cobalt, nickel, manganese, iron, copper, technetium, silver, rhenium, osmium, and gold, or may comprise platinum or rhodium alone or a single substance selected from the metal catalysts of the above group.

Among them, platinum/rhodium mixture is preferred. This is because rhodium is higher than platinum in heat resistance and presence of rhodium can further inhibit growth of catalyst particles.

In the present invention, the catalyst particles can be supported on the surface of particles of titanium dioxide by impregnating the surface of particles of titanium dioxide with the catalyst in the form of a metallic salt solution and heat treating the particles. The metallic salt solution includes, for example, nitric acid solution, hydrochloric acid solution, ammonium solution, cyanic acid solution, sulfuric acid solution, and the like. Furthermore, it is also possible to support catalyst particles on the surface of particles of titanium dioxide by mixing an organic solvent with particles of the metal oxide, molding the mixture into a bulk of a desired shape, impregnating this bulk with the above-mentioned catalyst solution, drying the bulk and then heat treating the bulk at a given temperature. Moreover, catalyst particles can be supported on the surface of particles of titanium dioxide by reduction decomposition process or by photoelectrodeposition process.

Calcination temperature is preferably about 800° C.-about 1300° C. This range of calcination temperature is necessary for obtaining a desired density of titanium dioxide sintered body as a final objective product and for reducing heat shrinkage of the product. About 800° C. is a lower limit for obtaining rutile crystal and about 1300° C. is an upper limit for being lower than sintering temperature.

In the present invention, it is preferred to carry out a heat treatment for stabilization after supporting catalyst particles on the surface of particles of titanium dioxide.

Catalyst particles are supported not only on the surface defects on the surface of particles of titanium dioxide, but also on the surface free from surface defects. In this case, the catalyst particles supported on the surface free from surface defects rapidly grow by temperature and exert a great influence on catalyst activity and so it is necessary to have saturated the growth of particles to some extent. This saturation temperature is higher than about 1000° C.

Since this heat treating temperature is included in the range of about 100° C.-about 1300° C. which is the range of sintering temperature for titanium dioxide particles, this heat treatment can be carried out simultaneously with sintering of particles of titanium dioxide.

Such heat treatment does not cause substantially no growth of catalyst particles bonded to surface defects of particles of titanium dioxide. On the surface of particles of titanium dioxide are supported fine catalyst particles of about 1 nm–about 30 nm and coarse catalyst particles of at least about 100 nm which have finished growing.

In the present invention, titanium dioxide sintered body ma not only be in the form of a thin film referred to hereinafter, but also be in the form of a bulk. Furthermore, particles of titanium dioxide as raw material may also be of anatase-type crystal structure. They are transformed to rutile-type crystal structure by the heat treatment.

Moreover, molding and sintering of particles of titanium dioxide can be simultaneously carried out by employing hot pressing method.

In the present invention, surface defects of particles of titanium dioxide can be increased and so catalyst particles which bond to the surface defects increases.

According to the present invention, growth of catalyst particles can be avoided and as a result, reduction of catalytic activity can be inhibited. Thus, the present invention exhibits excellent practical effect that sensitivity for detection of gas components can be stably maintained.

DESCRIPTION OF THE PREFERRED EMBODIMENTS

The present invention will now be explained by the following examples, it being understood that these examples are not intended to limit the invention thereto.

First, construction of titanium dioxide type oxygen concentration sensor to which the present invention is applied will be explained.

Figure 13:
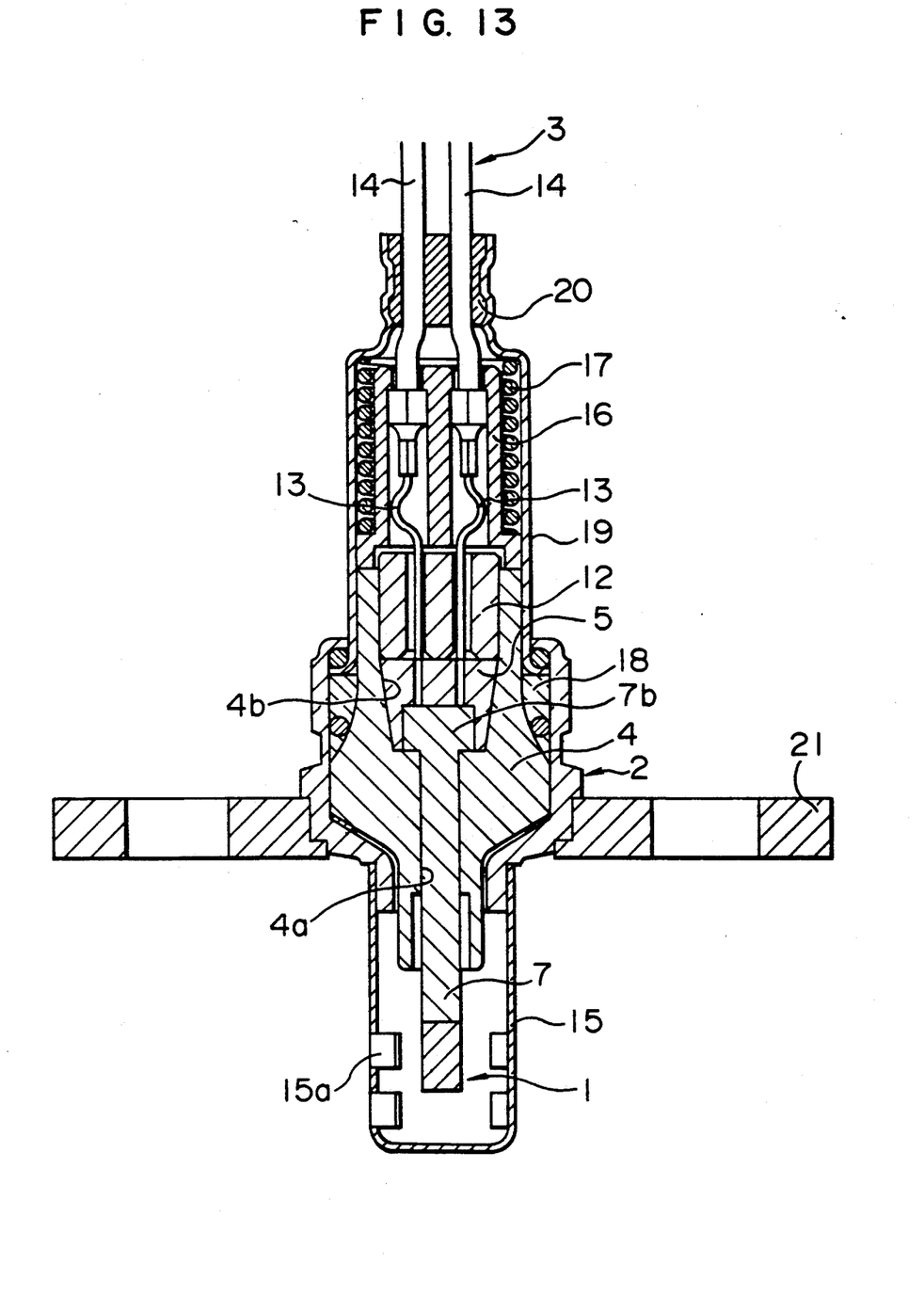
FIG. 13 is a general cross-sectional view.
Figure 14A:
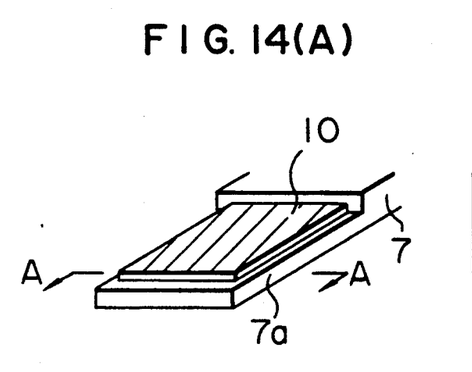
FIG. 14(a) is an oblique view of gas component detecting element part.
Figure 14B:
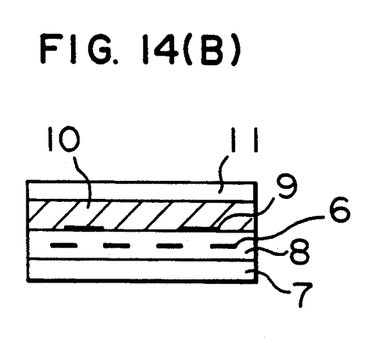
FIG. 14(b) is a cross-sectional view of the gas component detecting element part illustrated in FIG. 14(a), taken along line A—A of FIG. 14(a).

In FIG. 13 and FIG. 14(a) and (b), sensor comprises oxygen detecting part 1, housing 2 and terminal part 3 as in FIG. 13. Detecting part 1 has the construction as shown in FIG. 14(a) and (b) wherein lower level portion 7a (smaller thickness portion) is formed at the end of rectangular substrate 7 of aluminum oxide and thin film layer 8 of aluminum oxide which has therein heater wire 6 made by sintering platinum paste is formed on the lower level portion 7a. A pair of electrode wires 9 made by sintering platinum paste are formed on the thin film layer 8 and thin film type gas component detecting element 10 of the present invention is formed to cover the electrode wires 9. On this detecting element 10 is formed a porous protective layer 11 of titanium dioxide or aluminum oxide.

Substrate 7 having detecting element 10 is inserted into central hole 4a of small diameter of insulator 4 made of aluminum oxide and fixed housing 2 and is supported by collar 7b at an open end of central hole 4b of larger diameter of insulator 4. This supporting portion is sealed by adhesive 5, filled in central hole 4b. Insulator tube 12 made of aluminum oxide is placed above adhesive 5. The above-mentioned heater wire 6 and electrode wire 9 are electrically connected to lead wire 14 through metallic wire 13. To the lower end of housing 2 is welded a cylindrical metallic protective tube having many openings 15a so that it surrounds detecting element 10. In FIG. 13, 16 indicates a cylindrical support of aluminum oxide, 17 indicates a spring, 18 indicates a sealer comprising electrically insulating ceramic, 19 indicates a cylindrical metallic protective tube, 20 indicates a packing, and 21 indicates a mounting flange for fixing housing 2 to exhaust tube.

The production method of the present invention will be explained.

EXAMPLE 1

Particles of titanium dioxide having a specific surface area of 3.1 $m^2/g$ (first class grade chemical, rutile crystal) were calcined at about 1000° C. for 1 hour to obtain particles of titanium dioxide having a specific surface area of 1.5 $m^2/g$. Then, the calcined particles of titanium dioxide were charged in a pot made of aluminum oxide together with balls of aluminum oxide and were ground for 10 hours to obtain particles of titanium dioxide having a specific surface area of 3.0 $m^2/g$.

The above ground particles of titanium dioxide were impregnated with 5 wt % (based on the weight of titanium dioxide) of a mixed solution of chloroplatinic acid and rhodium chloride prepared so that molar fraction of platinum:rhodium was 9:1, then dried at 100° C. and heat treated at 400° C. for 1 hour.

10 wt % of ethyl cellulose binder was added to the particles of titanium dioxide which supported the catalyst comprising the mixture of platinum-rhodium to obtain a paste. This paste as a gas component detecting element was coated at a thickness of about 150 μm on a substrate as shown in FIG. 14(a) and (b) and sintered at about 1200° C. for 1 hour.

Figure 1:
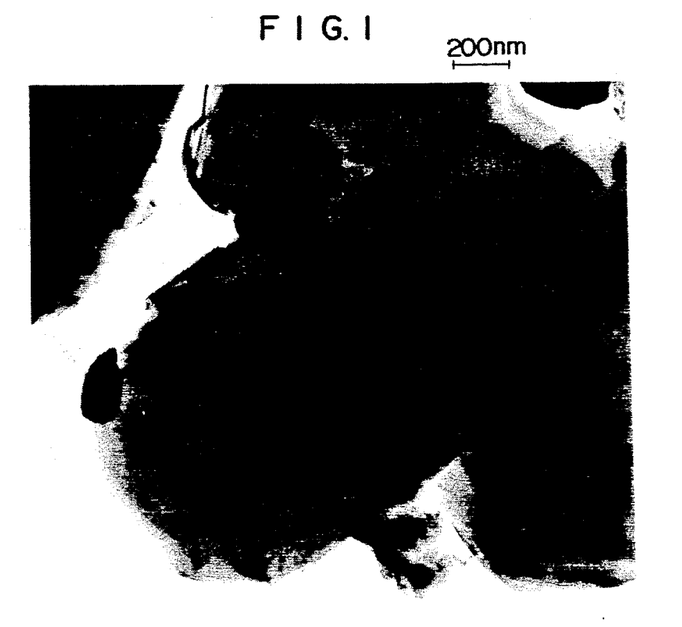
FIGS. 1-12 which are for explanation of the effect of the present invention are microphotographs which show particle structures of particles of titanium dioxide and catalyst particles.

TEM (transmission electron microscope) image of the detecting element part of the sensor provided with this gas component detecting element is shown in FIG. 1. In FIG. 1, the narrow rectangular image at the center shows particles of titanium dioxide and the small circular image deep in shadow shows catalyst particles. As can be understood from FIG. 1, there existed catalyst particles of more than about 100 μm which had finished growing due to the heat generated by sintering under high temperature of about 1200° C. for 1 hour and other particles which can grow were all within the above range of size.

Figure 2:
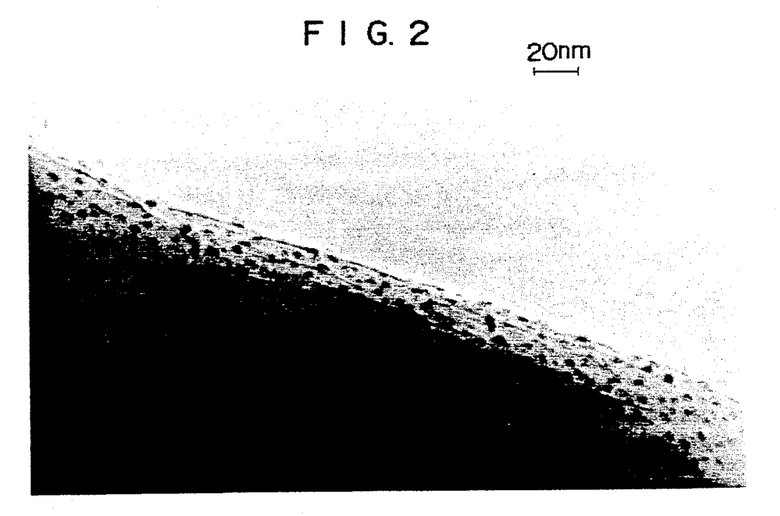

On the other hand, according to the image of high magnification shown in FIG. 2, catalyst particles of several μm (fine particles) were nearly uniformly deposited on the surface of particles of titanium dioxide.

Next, this sensor was subjected to endurance test under the following conditions.

Endurance Test Condictions

Figure 3:
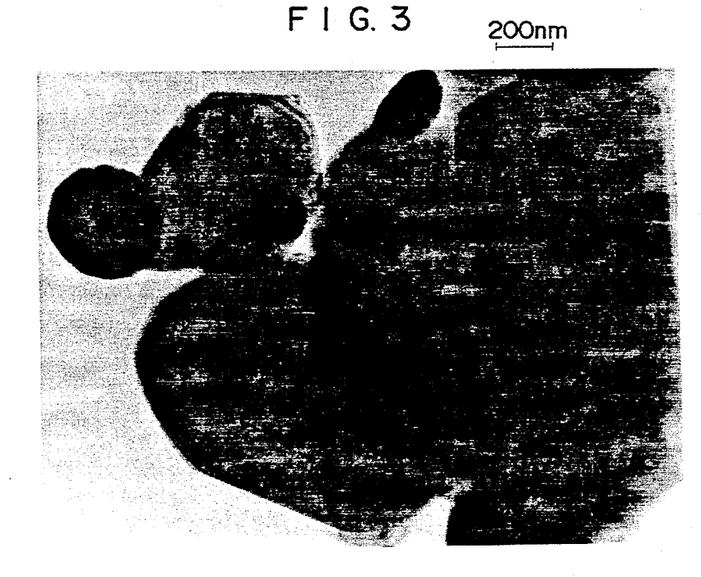
Figure 4:
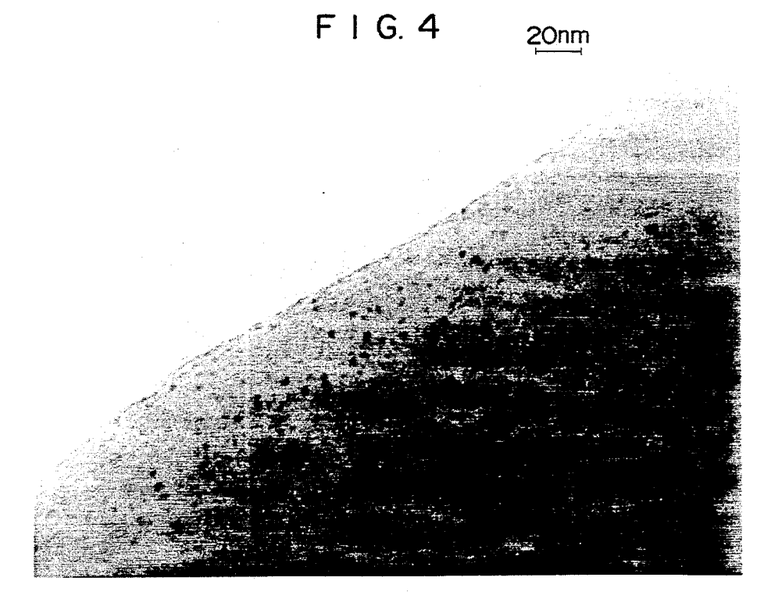

Engine used—4 cylinders, 4 cycles, 3,000 cc
Temperature of detecting element part of sensor—about 900° C.
Endurance test time—100 hours Results of the above endurance tests are shown in FIGS. 3 and 4. In FIG. 3, circular images of deep shadow indicate catalyst particles and images of larger size than the circular images indicate particles of titanium dioxide. In FIG. 4, images in the form of fine particles indicate catalyst particles. As can be seen from these FIGS. 3 and 4, they show substantially no change form the initial state of FIGS. 1 and 2.

Next, endurance test according to emission evaluation of exhaust gas was conducted under the following conditions.

Evaluation Conditions

Engine used—4 cylinders, 4 cycles, 1,600 cc
Temperature of detecting element part of sensor—about 900° C.

Figure 15:
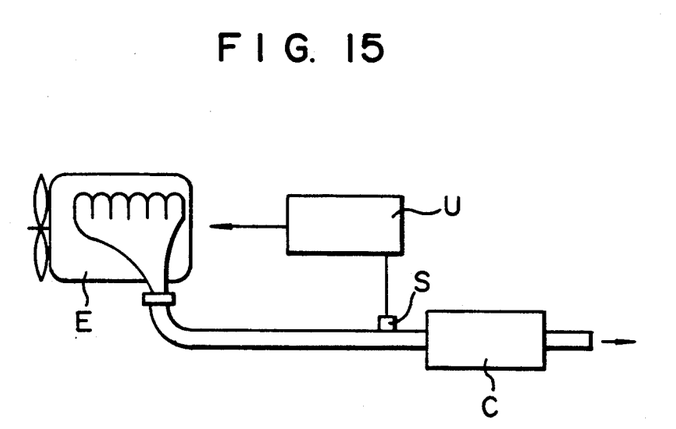
FIG. 15 is a schematic view of an exhaust system of engine for explanation of the present invention.

The emission evaluation of exhaust gas is conducted as follows: As shown in FIG. 15, gas component in exhaust gas from engine is detected by sensor S and the signal is processed by electrical control unit U to emit feed back signal to fuel feed part of engine E, thereby to adjust air fuel ratio (A/F) at the fuel feed part of engine and concentrations of hydrocarbon (HC), carbon monoxide (CO), and nitrogen oxide (NOx) after passing through ternary catalyst C at the state of the adjusted air fuel ratio (A/F) are measured. Control point in electrical control unit is a value of theoretical air fuel ratio $\lambda = 1.0$.

Figure 16:
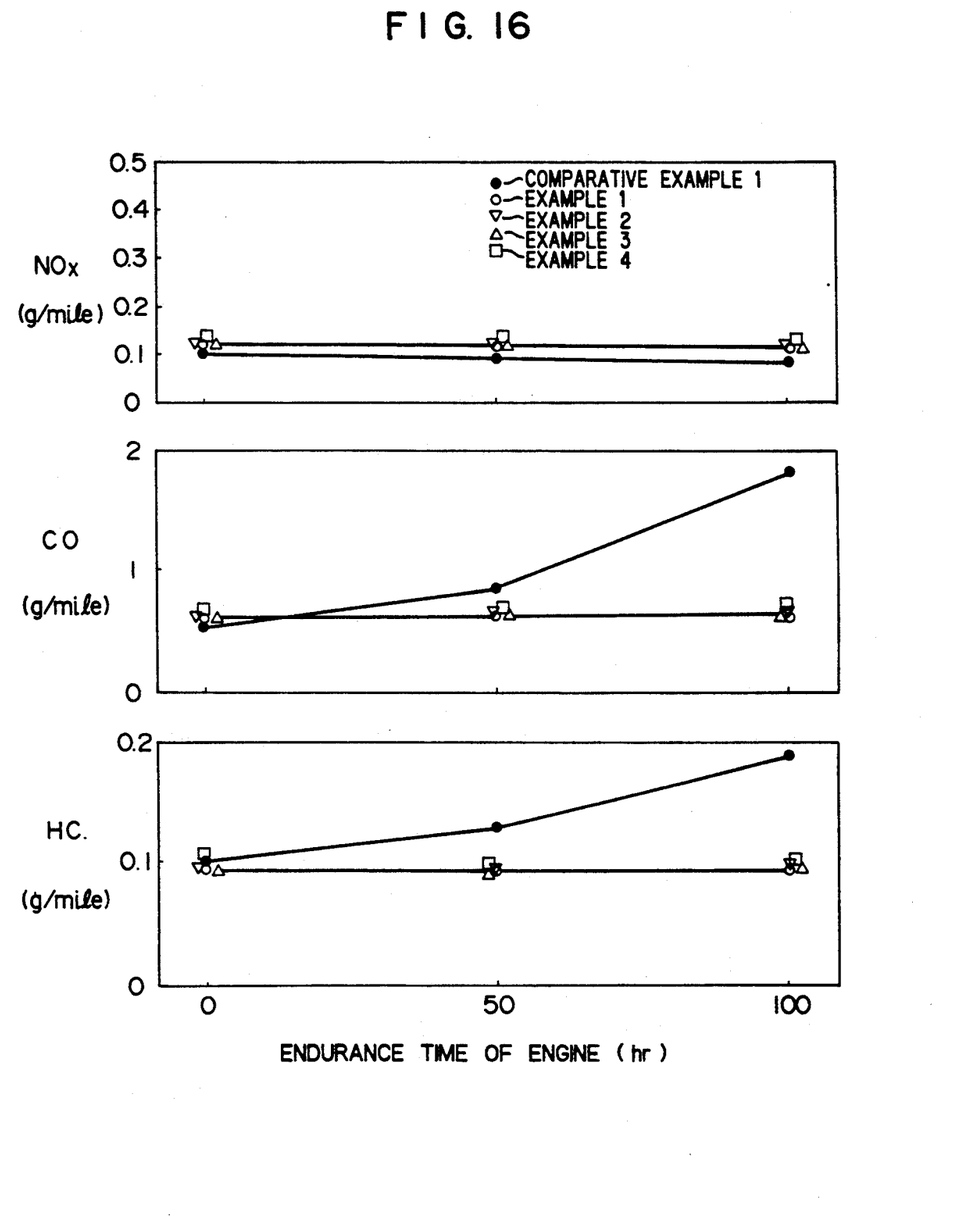
FIG. 16 show characteristic graphs for explanation of effect of the present invention.

The results are shown in FIG. 16. As can be seen from FIG. 16, no change of emission was recognized in the sensor of this Example.

From the above results, it can be seen that according to this Example, the catalyst particles deposited onto the surface of particles of titanium dioxide do not move even by the heat under high temperature and as a result, stable catalytic activity can be obtained.

EXAMPLE 2

Particles of titanium dioxide having a specific surface area of 3.1 $m^2/g$ (first class grade chemical, rutile crystal) were calcined at about 1300° C. for 1 hour to obtain particles of titanium dioxide having a specific surface area of 0.8 $m^2/g$. Then, the calcined particles of titanium dioxide were charged in a pot made of aluminum oxide together with balls of aluminum oxide and were ground for 10 hours to convert the specific surface area of the particles of titanium dioxide to 2.0 $m^2/g$.

Then, the same catalyst as used in Example 1 was supported on the particles of titanium dioxide in the same manner as in Example 1 and a gas component detecting element was formed on a substrate as in FIG. 14(a) and (b) in the same manner as in Example 1.

Figure 5:
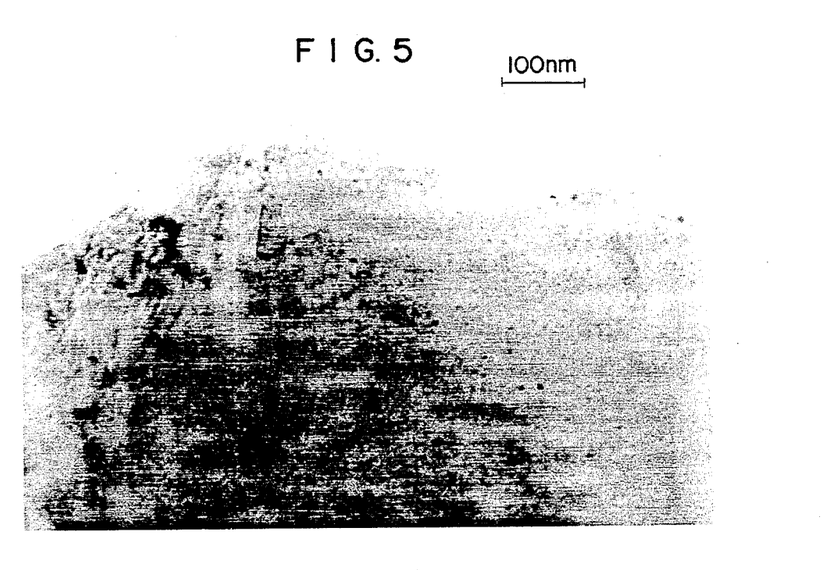

TEM (transmission electron microscope) image of the detecting element part of the sensor provided with the gas component detecting element obtained in this Example 2 is shown in FIG. 5. In FIG. 5, images in the form of fine particles indicate catalyst particles. Furthermore, TEM image of the detecting element part which had been subjected to the same endurance test as in Example 1 is shown in FIG. 6, wherein images in the form of fine particles indicate the catalyst particles.

Furthermore, endurance test according to emission evaluation of exhaust gas was conducted under the same conditions as in Example 1. The results are shown in FIG. 16.

Figure 6:
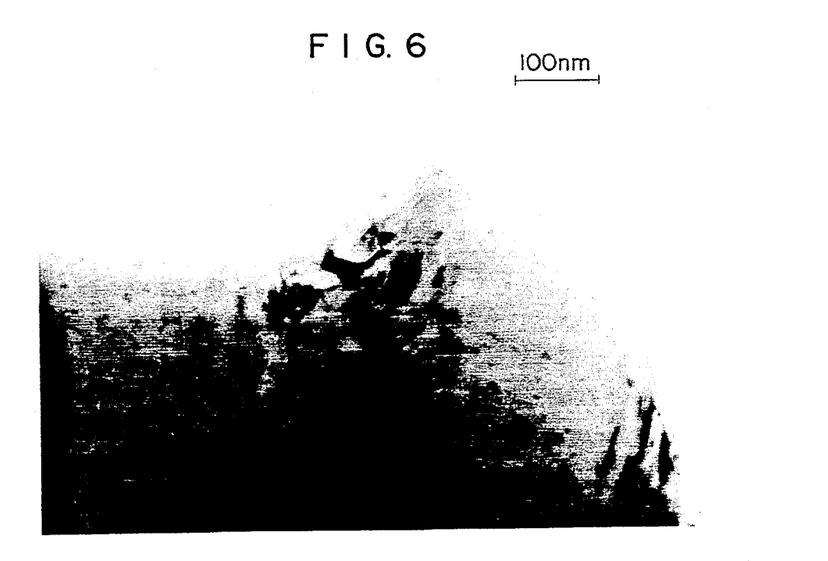

It can be seen from FIG. 5, FIG. 6, and FIG. 16 that the number of catalyst particles in the form of fine particles was somewhat smaller than that in Example 1, but catalytic activity nearly equal to that in Example 1 was obtained.

EXAMPLE 3

A gas component detecting element was obtained in the same manner as in Example 1 except that amount of the catalyst supported was 2 wt % or 8 wt % in place of 5 wt %.

TEM image of detecting element part of a sensor having the gas component detecting element obtained above was examined to find that it was nearly the same as that of FIG. 2 and the catalyst particles were fine. Furthermore, there was substantially no difference in the fineness depending on amount of the catalyst supported.

Endurance test according to emission evaluation of exhaust gas was conducted under the same conditions as in Example 1. The results are shown in FIG. 16.

It can be seen from FIG. 16 that there was obtained catalytic activity nearly equal to that obtained in Example 1 where amount of the catalyst was 5 wt %. According to experiments by the inventors, when amount of the catalyst supported is more than 20 wt %, sintering of particles of titanium dioxide is hindered and besides cost increases and thus the supporting amount is preferably not more than 20 wt %.

EXAMPLE 4

A gas component detecting element was obtained in the same manner as in Example 1 except that 5:5 was employed in place of 9:1 as molar fraction of platinum:rhodium of mixed solution of chloroplatinic acid and rhodium chloride to be supported as catalyst.

Figure 7:
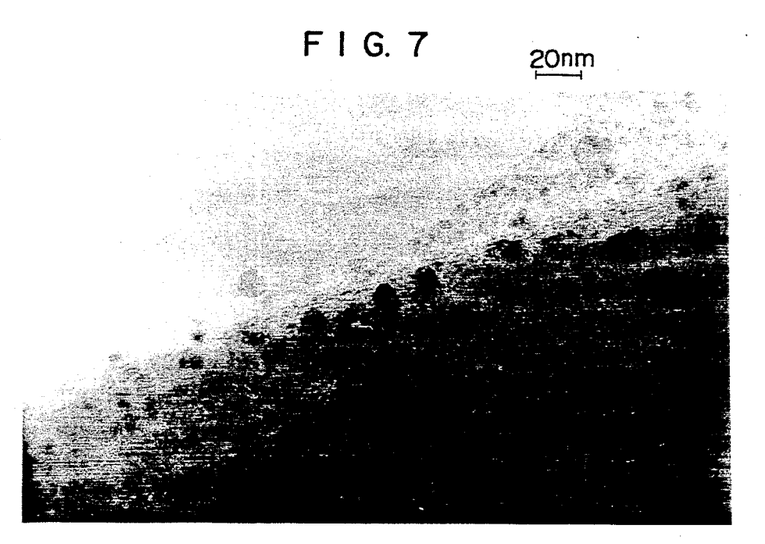

TEM image of detecting element part of a sensor having the gas component detecting element obtained in this Example 4 is shown in FIG. 7, wherein images in the form of fine particles indicate the catalyst particles.

Endurance test according to emission evaluation of exhaust gas was conducted under the same conditions as in Example 1. The results are shown in FIG. 16.

It can be seen from FIG. 7 that there was no difference in state of fineness of catalyst particles depending on amount of catalyst supported. Furthermore, as can be seen from FIG. 16, catalytic activity obtained was nearly the same as that in Example 1.

COMPARATIVE EXAMPLE 1

Particles of titanium dioxide having a specific surface area of 3.1 $m^2/g$ (first class grade chemical, rutile crystal) were calcined at about 1000° C. for 1 hour to obtain particles of titanium dioxide having a specific surface area of 1.5 $m^2/g$. Then, the calcined particles of titanium dioxide were charged in a pot made of aluminum oxide together with balls of aluminum oxide and were ground for 10 hours to convert the specific surface area of particles of titanium dioxide to 3.0 $m^2/g$.

10 wt % of ethyl cellulose binder was added to the above particles of titanium dioxide to obtain a paste. This paste as a gas component detecting element was coated at a thickness of about 150 $\mu$m on a substrate as shown in FIG. 14(a) and (b) and sintered at about 1200° C. for 1 hour. Specific surface area of the thus sintered particles of titanium dioxide was 0.9 $m^2/g$.

The resulting titanium dioxide sintered body was impregnated with a mixed solution of chloroplatinic acid and rhodium chloride prepared so that molar fraction of platinum:rhodium was 9:1 in an amount of 5 wt % based on the weight of the sintered body. Then, the sintered body was dried at 100° C. and baked at 800° C. for 1 hour to support the catalyst on the sintered body.

Figure 8:
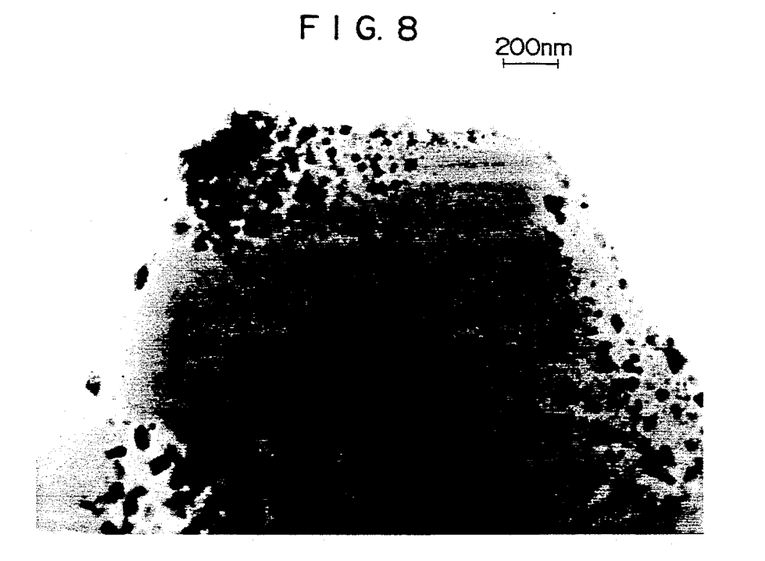

TEM image of the detecting element part of a sensor having the gas component detecting element is shown in FIG. 8. In FIG. 8, the images in the form of fine particles of deep shadow indicate the catalyst particles.

Figure 9:
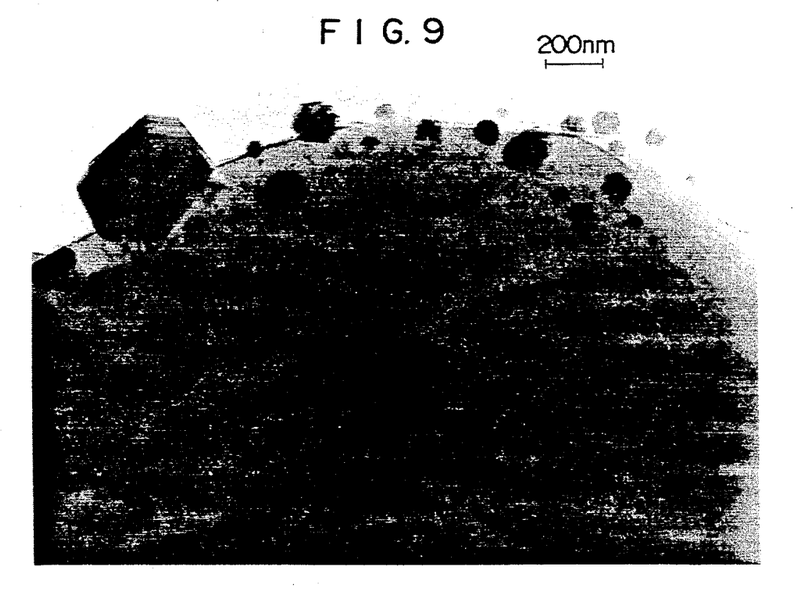
Figure 10:
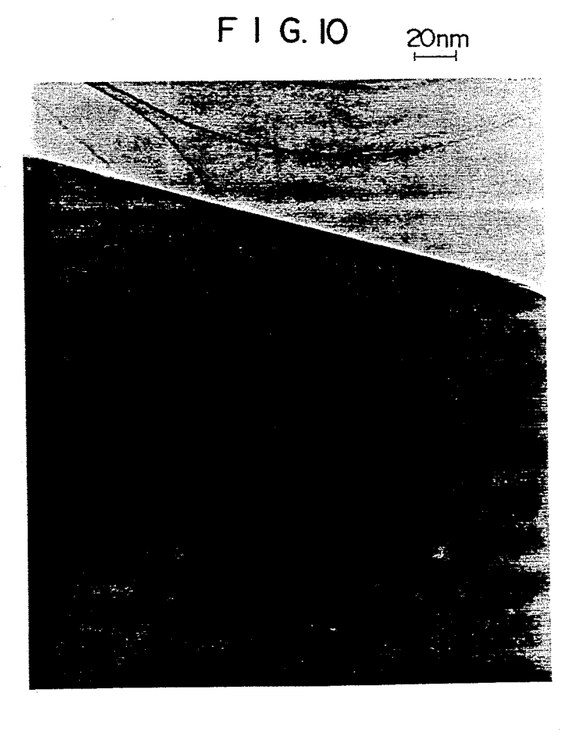

This sensor was subjected to the same endurance test as in Example 1 and TEM image of the detecting element part which had been subjected to the endurance test is shown in FIG. 9 and image of higher magnification is shown in FIG. 10. In FIG. 9, images in the form of fine particles deep in shadow indicate the catalyst particles. In FIG. 10, the surface of the oblique line indicates the surface of particles of titanium dioxide and streaks positioned above the oblique line indicate mesh of microgrid of TEM.

As can be seen from FIG. 9, catalyst particles in the form of fine particles of several nm in FIG. 8 disappeared by growth of particles and grew to particles of several ten nm-several hundreds nm. Furthermore, as can be seen from FIG. 10, no fine particles than the grown particles were observed in the high magnification image.

The same endurance test according to emission evaluation as in Example 1 was conducted to find change in control point as shown in FIG. 16.

COMPARATIVE EXAMPLE 2

Particles of titanium dioxide having a specific surface area of 3.1 m$^2$/g (first class grade chemical, rutile crystal) were calcined at about 1300° C. for 1 hour to obtain particles of titanium dioxide having a specific surface area of 0.8 m$^2$/g.

The above particles of titanium dioxide were impregnated with 5 wt % (based on the weight of titanium dioxide) of a mixed solution of chloroplatinic acid and rhodium chloride prepared so that molar fraction of platinum:rhodium was 9:1, then dried at 100° C. and heat treated at 400° C. for 1 hour. 10 wt % of ethyl cellulose binder was added to the particles of titanium dioxide which supported catalyst comprising a mixture of platinum-rhodium to obtain a paste. This paste as a gas component detecting element was coated at a thickness of about 150 μm on a substrate as shown in FIG. 14 (a) and (b) and sintered at about 1200° C. for 1 hour.

Figure 11:
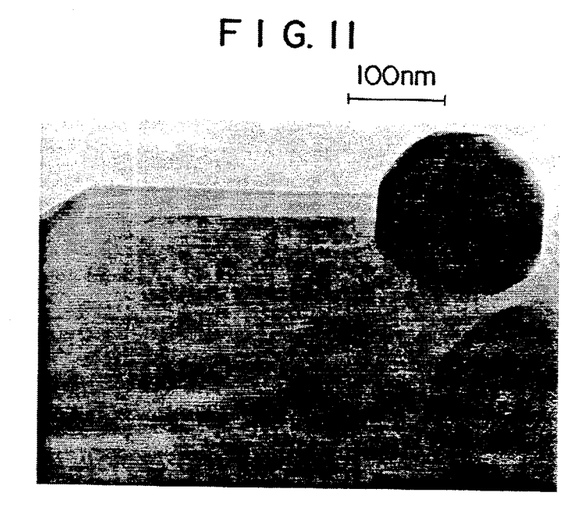

TEM image of detecting element part of a sensor provided with this gas component detecting element is shown in FIG. 11. In FIG. 11, the circular images deep in shadow in the right portion indicate catalyst particles. High magnification image is shown in FIG. 12.

Figure 12:
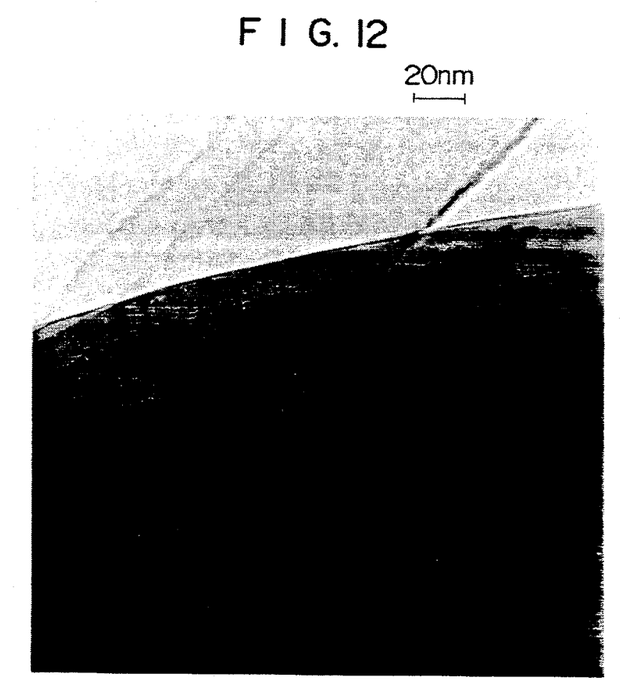

As can be seen from FIG. 11 and FIG. 12, since no catalyst particles in the form of fine particles were deposited and catalytic activity was low, the same emission evaluation as in Example 1 was not able to be conducted. This is because surface defects on the particles of titanium dioxide disappeared due to the heat treatment at high temperature of about 1300° C. and the particles of titanium dioxide were not subjected to treatment to reproduce surface defects by grinding the particles as in Examples 1-4.

What is claimed is:

1. A detector of the type which has a gas component detecting element comprising a sintered body of particles of a metal oxide which changes in its electrical resistance depending on relative atmosphere of combustible components in an exhaust gas, catalyst particles being supported on the particles of metal oxide, wherein the catalyst particles comprise fine catalyst particles of about 1 nm-about 30 nm and coarse catalyst particles of at least about 100 nm, the fine catalyst particles and the coarse catalyst particles are supported on the particles of the metal oxide, the element being formed by the steps of:
   preparing particles of a metal oxide,
   calcining the particles of the metal oxide,
   subjecting the calcined particles from said calcining step to a treatment for a enlarging a specific surface area of the calcined particles and to increase surface defects thereof,
   supporting catalyst particles on the surface of the particles subjected to the enlargement treatment in said subjecting step,
   sintering the particles which support the catalyst particles; and
   forming the gas component detecting element from the sintered particles.

2. A detector according to claim 1, wherein the particles of the metal oxide are titanium dioxide and the catalyst particles comprise a mixture of platinum-rhodium.

3. A gas component detecting element for a detector which has a sintered body of particles of a metal oxide which changes in its electrical resistance depending on relative atmosphere of combustible components in an exhaust gas, having catalyst particles supported on the surface of particles of the metal oxide, the element being formed by a method comprising the following steps:
   preparing particles of a metal oxide,
   calcining the particles of the metal oxide,
   subjecting the calcined particles from said calcining step to a treatment for a enlarging a specific surface area of the calcined particles and to increase surface defects thereof,
   supporting catalyst particles on the surface of the particles subjected to the enlargement treatment in said subjecting step,
   sintering the particles which support the catalyst particles; and
   forming the gas component detecting element from the sintered particles.

4. A gas component detecting element for detectors which comprises a sintered body of particles of titanium dioxide which changes in its electrical resistance depending on relative atmosphere of combustible components in an exhaust gas, catalyst particles being supported on the surface of the particles of titanium dioxide, the detector being formed by a method comprising the following steps:
   preparing the particles of titanium dioxide,
   calcining the particles of titanium dioxide,
   subjecting the calcined particles from said calcining step to a grinding treatment so that a ratio of specific surface area $A_1$ of the calcined particles before being subjected to grinding and a specific surface area $A_2$ of the particles after being subjected to grinding satisfies the relation $A_1/A_2 < 1.0$, and to thereby increase surface defects thereof,
   supporting catalyst particles on surfaces of the particles subjected to the grinding treatment, and sintering the particles which support to the catalyst particles; and
   forming the gas component detecting element from the sintered particles.

5. A gas component detecting element for detectors comprising an electrical insulating substrate and the gas component detecting element having a sintered body of particles of titanium dioxide which changes in electrical resistance depending on a relative atmosphere of combustible components in an exhaust gas, catalyst particles being supported on the surface of the particles of titanium dioxide, the element being formed by the following steps:
   preparing the particles of titanium dioxide,
   calcining the particles of titanium dioxide,
   subjecting the calcined particles to a grinding treatment so that a ratio of a specific surface area $A_1$ of the specific surface area $A_2$ of the particles after being subjected to grinding satisfies the relation $A_1/A_2 < 1.0$,
   impregnating the particles of titanium dioxide subjected to the grinding treatment with a mixed solution of chloroplatinic acid and rhodium chloride,
   adding an organic binder to the particles of titanium dioxide impregnated with the mixed solution to obtain a paste,
   providing the paste including particles of titanium dioxide on an electrical insulating substrate in the form of a film at a given thickness, and
   sintering the particles of titanium dioxide provided on the substrate at 800°-1300° C.

* * * * *